United States Patent [19]

Ambrose et al.

[11] Patent Number: 5,392,590
[45] Date of Patent: Feb. 28, 1995

[54] PACKAGING AND METHODS FOR REDUCING ODORS AND STRENGTH LOSS CAUSED BY THE IRRADIATION OF POLYOLEFIN-BASED PRODUCTS

[75] Inventors: Julia T. Ambrose, Marietta; Charles E. Bolian, II, Buford, both of Ga.; Stephen E. Ellis, Andover; Jeffery H. Worthington, Saugus, both of Mass.

[73] Assignee: Kimberly-Clark Corporation, Neenah, Wis.

[21] Appl. No.: 249,097

[22] Filed: May 18, 1994

Related U.S. Application Data

[63] Continuation of Ser. No. 994,792, Dec. 21, 1992, abandoned.

[51] Int. Cl.$^6$ ............................................. B65B 55/02
[52] U.S. Cl. ................................. 53/425; 53/111 RC; 53/428
[58] Field of Search ............... 53/425, 426, 431, 428, 53/111 RC, 111 R; 422/23, 22, 28, 33

[56] References Cited

U.S. PATENT DOCUMENTS

| | | | |
|---|---|---|---|
| 2,904,392 | 9/1959 | Pomerantz et al. | 21/54 |
| 2,917,878 | 12/1959 | Carnarius et al. | 53/426 |
| 3,043,067 | 7/1962 | Rynkiewicz et al. | 53/426 |
| 3,194,668 | 7/1965 | Schlein et al. | 99/171 |
| 3,370,915 | 2/1968 | Sperberg | 23/4 |
| 3,625,888 | 12/1971 | Ballwin | 252/8.55 D |
| 3,688,985 | 9/1972 | Engel | 239/54 |
| 3,728,839 | 4/1973 | Glick | 53/21 FC |
| 4,110,185 | 8/1978 | Williams et al. | 204/159.2 |
| 4,230,595 | 10/1980 | Yamaji et al. | 252/188 |
| 4,274,932 | 6/1981 | Williams et al. | 204/159.2 |
| 4,317,742 | 3/1982 | Yamiji et al. | 252/188 |
| 4,391,080 | 7/1983 | Brody et al. | 53/426 |
| 4,431,497 | 1/1984 | Rekers | 204/159.2 |
| 4,460,445 | 7/1984 | Rekers | 204/159.2 |
| 4,467,065 | 8/1984 | Williams et al. | 524/296 |
| 4,497,406 | 2/1985 | Takanashi | 206/438 |
| 4,501,789 | 2/1985 | Shah et al. | 428/274 |
| 4,537,305 | 8/1985 | Takanashi | 206/438 |
| 4,547,191 | 10/1985 | Ichikawa et al. | 604/251 |
| 4,617,230 | 10/1986 | Shah et al. | 428/288 |
| 4,686,125 | 8/1987 | Johnston et al. | 428/35 |
| 4,692,361 | 9/1987 | Johnston et al. | 428/35 |
| 4,709,819 | 12/1987 | Lattuada et al. | 206/524.8 |

(List continued on next page.)

FOREIGN PATENT DOCUMENTS

| | | |
|---|---|---|
| 218003 | 4/1987 | European Pat. Off. |
| 0328336 | 8/1989 | European Pat. Off. |
| 0407198 | 1/1991 | European Pat. Off. |
| 0457048 | 11/1991 | European Pat. Off. |
| 2025430 | 11/1972 | France |
| 1230950 | 5/1971 | United Kingdom |

OTHER PUBLICATIONS

"Material Design of Radiation Resistant Polypropylene" Part II–Importance of the Smectic Structure Produced by Quenching Treatment–by S. Nishimoto et al., Polymer Degradation and Stability, 14 (1986) pp. 199–208.

"Importance of the Amorphous Fraction of Polypropylene In The Resistance to Radiation–Induced Oxidative Degradation" by T. Kagiya, et al., Polymer Degradation and Stability, 12 pp. 261–275 (1985).

Primary Examiner—James F. Coan
Attorney, Agent, or Firm—William D. Herrick

[57] ABSTRACT

The invention provides a method for reducing or eliminating the odors commonly produced by the sterilization of polyolefin-based products by gamma radiation. In addition, the invention also provides a method for minimizing the amount of fabric strength loss associated with the irradiation process and a method for actually increasing the fabric strength of a polyethylene that has been irradiated. Both the reduction in odors and the minimization of strength or increase in polyolefin strength are achieved in methods comprising the use of an oxygen scavenger. The invention further includes the use of non-gamma stabilized polyolefins. The polyolefinic product may also include an odor mask that may be used to mask any residual odor.

25 Claims, 1 Drawing Sheet

U.S. PATENT DOCUMENTS

| | | | |
|---|---|---|---|
| 4,740,402 | 4/1988 | Maeda et al. | 428/35 |
| 4,769,175 | 9/1988 | Inoue | 252/188.28 |
| 4,851,130 | 7/1989 | May | 210/750 |
| 4,856,650 | 8/1989 | Inoue | 206/204 |
| 4,877,664 | 10/1989 | Maeda et al. | 428/35.9 |
| 4,879,127 | 11/1989 | Liu et al. | 426/325 |
| 4,931,230 | 6/1990 | Krueger et al. | 264/6 |
| 4,992,410 | 2/1991 | Cullen et al. | 502/407 |
| 5,001,176 | 3/1991 | Nakazima | 524/48 |
| 5,014,494 | 5/1991 | George | 53/425 |
| 5,041,483 | 8/1991 | Burch | 524/274 |
| 5,064,698 | 11/1991 | Courtright et al. | 428/35.4 |
| 5,075,362 | 12/1991 | Hofeldt et al. | 524/72 |

PACKAGING AND METHODS FOR REDUCING ODORS AND STRENGTH LOSS CAUSED BY THE IRRADIATION OF POLYOLEFIN-BASED PRODUCTS

This application is a continuation of application Ser. No. 07/994,792, entitled "Packaging and Methods For Reducing Odors and Strength Loss Caused by the Irradiation of Polyolefin-Based Products" and filed in the U.S. Patent and Tradmark Office on Dec. 21, 1992, and now abandoned.

FIELD OF THE INVENTION

The invention generally concerns the use of an oxygen scavenger to reduce or eliminate the undesirable side effects associated with the gamma irradiation of polyolefin-based products.

BACKGROUND OF THE INVENTION

Various fields of use require the use of sterilized polyolefin-based clothing, equipment and tools. For example, it is well known that the operating environments of medical personnel, dental personnel, chemical research personnel, biotech personnel, and other like areas of use all require the use polyolefin-based workwear products that have been sterilized prior to use.

In the past, ethylene oxide has been used to sterilize polyolefin-based products such as medical fabrics that are used as surgical gowns and drapes. However, the potentially hazardous nature and high cost of ethylene oxide sterilization have caused the medical community to consider different sterilization methods. One effective method of sterilization has been the use of gamma irradiation.

Although sterilization by gamma irradiation of polyolefin-based products and equipment has been successful, there remain at least two very undesirable side effects caused by the irradiation process. The first undesirable side effect has been a resulting odor that is so extreme that it renders the gamma irradiated polyolefin-based product undesirable for many uses. The second undesirable side effect has been a noticeably decreased strength of the irradiated polyolefin products. In fact, the irradiation process has been known to decrease a polyolefin-based product's tear strength by as much as 65% of its non-irradiated tear strength.

It has been shown that the cause for the undesirable odor and the loss in fabric strength is a free radical process that occurs when the polyolefins of the product are exposed to gamma radiation in the presence of oxygen. In polyolefin-based products, this process essentially breaks chemical bonds that hold a polyolefin chain together and creates free radicals. This breaking of the polyolefin backbone causes the polyolefin to lose strength proportional to the radiation dosage. The formed radicals are able to recombine with the oxygen in the air, producing short chain acids, oxygenated compounds, such as that become trapped in the product. Butyric acid, one of the acids formed, is a primary suspect in causing the odor.

In efforts to combat these two undesirable side effects, others have tried various processes. For example, U.S. Pat. No. 3,194,668, to Schein and Liberte teaches a process for preparing radiation-stabilized polyethylene products that adds an amount of 2, 2'-methylene-bis-(4-ethyl-6-t-butyl phenyl) to the polyethylene prior to its being sterilized. U.S. Pat. No. 4,501,789 to Burch teaches the pretreatment of polypropylene products with rosin esters, anti-oxidants or prodegradants to reduce the odor caused by the gamma-irradiation of polypropylene products. Further, U.S. Pat. Nos. 4,501,789 and 4,617,230 to Shah, et al. teach the sterilization treatment of polyolefin-based latex non-woven fabrics with an odor inhibition agent selected from amine-type antioxidants and hindered phenols.

Although the above-described patents have taught methods that marginally reduce the odor associated with the gamma irradiation of polyolefin-based products, none has adequately reduced the odor or minimized the reduction in tear strength resulting from the irradiation treatment. A need therefore exists for a method for minimizing or eliminating the odor that is associated with the gamma irradiation of polyolefin-based products. A need further exists for a method that not only reduces the odor, but also minimizes any decrease in the strength of the polyolefin product that is due to the gamma irradiation. Ideally, this need will be satisfied by a method that not only minimizes the polyolefin strength loss, but in fact, actually increases the strength of the post-irradiated polyolefin product.

It is therefore an object of the invention to provide a method for reducing both the odor and the polyolefin strength loss associated with the gamma irradiation process.

SUMMARY OF THE INVENTION

The invention comprises a method for reducing oxygen in packaging of polyolefin-based products with an oxygen scavenger prior to sterilization by gamma radiation such that both the odor associated with the irradiation of the polyolefin-based product is eliminated or reduced and the post-irradiation strength of the polyolefin-based product is either only minimally decreased or actually increased.

The polyolefin-based products of the present invention may be either copolymers, such as copolymers of propylene and ethylene, or homopolymers consisting of, for example, 100% polypropylene, or blends with other polymers, both thermoplastic and non-thermoplastic.

The oxygen scavengers of the present invention include iron compounds, copper compounds, vitamin C based compounds, and other like compounds. The product, i.e., fabrics, etc., is generally of the polyolefin family, in particular, polypropylene, polyethylene, or copolymers thereof, and including blends with these polyolefins.

The invention also comprises carrier means such as a cellulose-based card that carries or has been treated with an oxygen scavenger and a method for using the treated card as a means for reducing or eliminating the odor and the post-irradiation strength loss of the irradiated polyolefin-based products. In this method, the card may be packaged with the polyolefin-based product inside the package to be sterilized. When the polyolefin-based product is in the form of a polyolefin-based fabric type material, such as a surgical gown, the card may additionally function as a tie card that allows the user to aseptically tie the gown.

The invention further includes an odor mask and an odor scavenger that may be used in conjunction with the oxygen scavenger.

BRIEF DESCRIPTION OF THE DRAWING

The Figure illustrates a package in accordance with the invention containing an oxygen scavenger.

DETAILED DESCRIPTION OF THE PREFERRED EMBODIMENT

Figure 1:
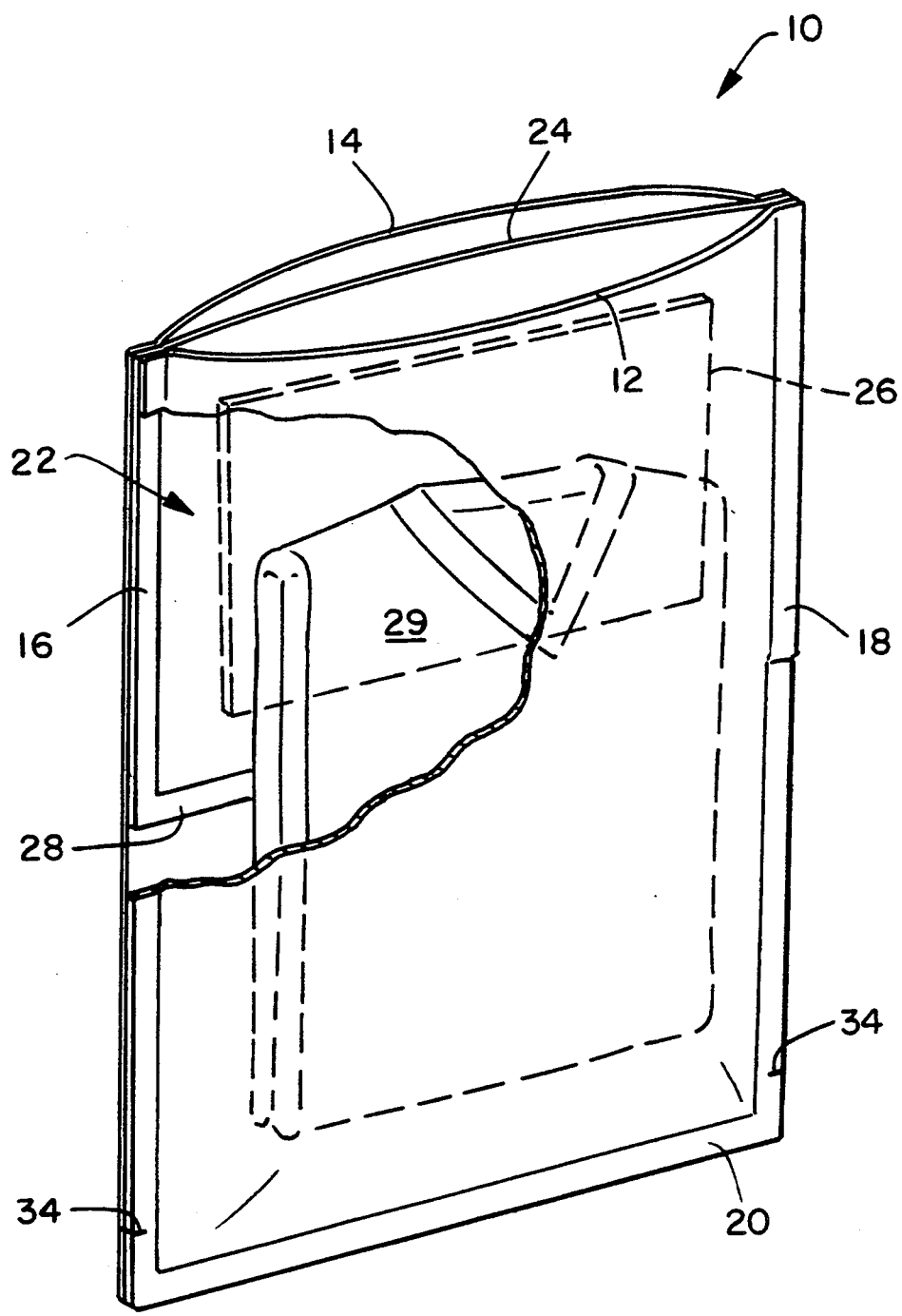

The inventors of the present invention have discovered that the introduction of an oxygen scavenger inside the packaging of a polyolefin-based product significantly reduces or eliminates the associated odor, and either minimizes the reduction in strength, or actually increases the strength of the polyolefin-based product after the package and its contents have been sterilized. The oxygen scavenger removes the oxygen that is present in the packaging prior to gamma irradiation. When the product is irradiated, some of the bonds in the polyolefin chains are broken and combine with available oxygen, which leads to more chain scission, thereby weakening the product. With the present method, the product is irradiated, causing the breakage of some of the polyolefin chains, but there is little or no oxygen to combine with the bonding sites in the broken polyolefin chains. The available bonding sites in the polyolefin chains are therefore free to recombine with one another instead of with oxygen in the package such that the majority of the strength of the irradiated product is maintained. In the case of polyethylene the strength of the irradiated polyolefin product may actually be greater than the pre-radiation strength of the product. It is believed that the strength increase is attributable to the recombination of the original chains plus cross-linking with other parallel polyolefin chains. In the presence of oxygen, the amount of cross-linking phenomenon which occurs is reduced due to a much faster reaction with oxygen. The minimization of the potential for the formation of oxygenated compounds, such as short-chain organic acids, with consequent reduction or elimination of odors associated therewith, also comprises a feature of the present invention, as do products which exhibit such characteristics.

In addition, the oxygen scavenger also functions to reduce or eliminate the odor associated with the irradiated product as there is minimal oxygen present to combine with the radicals produced by the irradiation. The present invention is primarily directed to a polyolefin-based product, such as a nonwoven fabric. The fabrics of the present invention are generally selected from the polyolefin family. More specifically, the polyolefins may either be homopolymers or copolymers. The preferred homopolymer is polypropylene, and the preferred copolymer is a propylene/ethylene copolymer. The amount of propylene in the copolymer may range from 90% to 100%, and the amount of ethylene in the copolymer may range from 0 to 10%. It should be appreciated that as the amount of ethylene is increased, the flexibility of the fabric being produced will also be increased. The inventors have therefore determined that the preferred copolymer is 97% propylene and 3% ethylene.

The process and method for making the polyolefin-based fabrics are well known in the art. See for example U.S. Pat. Nos. 4,041,203 and 4,340,563, herein incorporated by reference.

The weight of the produced fabric, represented in ounces per square yard is normally determined by the intended use thereof. For example, if the fabric is to be used as a vehicle cover, the weight of the fabric should generally be in the range of 7.20 ounces per square yard. If the fabric is to be used as a diaper liner, the weight of the fabric should generally be in the range from 0.3 ounces per square yard to 0.8 ounces per square yard. For surgical gowns, the fabric weight should range from 0.8 ounces per square yard to 3.0 ounces per square yard.

The preferred polyolefin-based fabric of the present invention is "SMS" which may be obtained from the Kimberly-Clark Corporation. SMS is a "spun-bond, melt-blown, spun-bond" polyolefin-based laminate fabric in which the "spun-bond" layers represent continuous larger polyolefin fibers that impart strength and a "melt-blown" layer that is comprised of smaller polyolefin fibers that act as a barrier. In combination therefore, the SMS fabric is a resilient and resistant fabric that is ideal for medical fabrics such as surgical gowns. SMS is also particularly useful, for example, as a surgical gown because it has good liquid and particle barrier properties, high breathability, low lint, and is resistant to ignition.

A gamma stabilizer, such as a benzoate ester, may be incorporated into the polyolefin prior to polyolefin extrusion. In the past, it has generally been believed that a gamma stabilizer must be added to the polyolefin in order to stabilize the polyolefin for the gamma irradiation process. This step was taken in an effort to minimize polyolefin strength loss and decrease odors. However, the inventors of the present invention have discovered that the use of a gamma stabilizer is not necessary in order to minimize polyolefin strength loss and odor. As described in the examples, the present invention has been found to minimize strength loss in polypropylene and copolymers without a gamma stabilizer. In the case of polyethylene, the present invention has actually been shown to increase the polyolefin strength. The inventors of the present invention have also determined that the gamma stabilizer is not needed to reduce the odor associated with the gamma irradiation process. Nevertheless, a suitable gamma stabilizer may be incorporated into the polyolefin prior to extrusion.

After the polyolefin-based product or fabric to be sterilized has been obtained, it is normally placed in an oxygen impermeable package. By "oxygen impermeable" it is meant that the material of construction exhibits a high barrier to oxygen transmission. Those skilled in the art will recognize such materials as, for example, saran or polyvinylidine chloride. In the case of surgical gowns and other medical fabrics, the gown is generally first placed in a wrap, and the wrapped gown is then placed in an oxygen impermeable package. Often, the individual package is then placed in a larger oxygen impermeable bag, for example a case liner, with several other individual packages.

Prior to sealing the individual packages containing the polyolefin product, an oxygen scavenger is inserted inside the package. The oxygen scavengers of the present invention include commercial grades of iron, such as iron filings, in combination with a catalyst. (See, for example, U.S. Pat. No. 4,992,410, herein incorporated by reference.) The preferred oxygen scavenger of the present invention is sold under the trademark FRESH-PAX®, obtained from Multiform Desiccants, Inc., of Buffalo, N.Y. Other oxygen scavengers that may be used in the present invention include copper-based compounds, vitamin C-based compounds, and other like compounds.

The oxygen scavenger should itself be packaged in an oxygen permeable package such that the oxygen scavenger is contained within its own package. See for example, U.S. Pat. No. 4,856,650, herein incorporated by reference. The amount of oxygen scavenger that is needed to remove the oxygen within a sealed package containing a polyolefin product or fabric will of course be dependent upon the volume of oxygen within that package.

Before sealing the package, it is possible to evacuate most of the oxygen from the package. However, this has not been shown to be as effective as the present invention and vacuum removal of oxygen is economically undesirable because of the cost and the increased production time caused by the additional vacuum step. In addition, vacuum packaging causes the final packaged product to be unsightly and the package is also very difficult to aseptically open. The present invention therefore does not require, and is actually designed to eliminate the need for vacuum packaging because a sufficient amount of oxygen scavenger is supplied to remove the amount of oxygen calculated to be present within the package. However, as will be apparent to those skilled in the art, vacuum packaging may be used in combination with the present invention to reduce the amount of scavenger required.

The amount of oxygen scavenger that is inserted into the oxygen impermeable package is generally ascertained by determining the amount of oxygen scavenger that will remove the amount of oxygen within the package prior to sterilization, usually 24 hours or less, to a level of 0.01% or 100 parts per million. The manufacturer of the oxygen scavenger typically indicates the amount of oxygen that can be removed in a certain time frame by the particular oxygen scavenger.

Rather than placing the oxygen scavenger within the individual package containing the polyolefin product or gown, the oxygen scavenger may also be placed within the larger oxygen impermeable sealable bag that contains several of the individually packaged gowns; however, that will necessitate an oxygen permeable bag for the individual gowns. Another embodiment contemplates the incorporation of the oxygen scavenger as a part of the sealable package itself. The oxygen scavenger is then suitably shielded until the package is ready for use.

In an alternate embodiment, the oxygen scavenger may be contained in, or mounted on, a carrier means such as a cellulosic fiber card. The oxygen scavenger may be incorporated into the card during its manufacture, attached to the card after the card is formed, or the card may be coated or saturated with an oxygen scavenger-containing solution.

In addition, the package of oxygen scavenger may be affixed to the card itself. An example of the above-described card that may be used to deliver the oxygen scavenger can be found in U.S. Pat. No. 3,843,971, herein incorporated by reference. It should be appreciated, as depicted in U.S. Pat. No. 3,843,971, that the card containing an oxygen scavenger may also be used as a means for its user to aseptically tie the polyolefin fabric gown.

In another preferred embodiment, an odor mask may be placed inside the individual polyolefin product or fabric packaging. Unlike the oxygen scavenger, which is believed to bond to free oxygen to prevent the oxygen from combining with the radicals released upon irradiation and which cause odors, the mask does not bond with the oxygen. Rather, the mask functions to release its own desirable scent such that it competes with and covers-up any undesirable odors that are not prevented by the oxygen scavenger. The mask can be baby powder-like or any other of the variety of fragrances that are well-known in the art. An odor mask should be incorporated into the polyolefin mixture prior to extrusion.

In another embodiment of the present invention, an odor scavenger may be used in conjunction with the previously described oxygen scavenger. The odor scavenger, such as activated carbon, is normally incorporated into the individual polyolefin product or fabric packaging by inserting an individually packaged odor scavenger inside the package containing the polyolefin product or fabric. It should however be noted that, alone, the odor scavenger will not adequately reduce the odor, and it will not minimize the polyolefin strength loss caused by the irradiation process. Other odor scavengers that may be used include molecular sieves such as the trademarked product ABSCENTS ® (obtainable from U.O.P.), baking soda compounds, zeolites, and other like compounds.

Once the desired components have been placed within the package, i.e. the polyolefin product or fabric with or without a gamma stabilizer and/or an odor mask, an oxygen scavenger, an odor scavenger, a card and/or a carrier means, the package is sealed by conventional means and then sterilized by gamma radiation. Methods for heat sealing oxygen impermeable packages are well known in the art.

Gamma irradiation techniques are also well-known in the art. For a general description of the gamma irradiation of polyolefin fibers see U.S. Pat. No. 5,041,483, which is herein incorporated by reference. Generally speaking, the amount of radiation necessary to sterilize the polyolefin product or gown is dependent upon the bioburden of the product. Additional factors include the density and configuration of the product to be sterilized. A likely range of irradiation is from 1.0 MRAD to 10.0 MRAD, more preferably from 1.5 MRAD to 6.0 MRAD.

The materials and methods used in carrying out the present invention may be more fully understood by reference to the following examples, which examples are not intended in any manner to limit the scope of the present invention.

EXAMPLE 1

The seven polyolefin-based fabrics listed in Table 1 were gamma stabilized with 1% American Cyanamide 2908 type stabilizer. These fabrics had no odor mask unless stated otherwise. The test comprised the use of three 12 square yard samples of each fabric. One sample of each fabric was kept as a control sample. The other two samples of each fabric were irradiated at 6 MRADS. One sample of each fabric to be irradiated did not have any oxygen scavenger. The other sample of each fabric to be irradiated did contain an oxygen scavenger.

TABLE I

FABRIC IDENTIFICATION KEY

A. 0.8 oz/yd$^2$ polyethylene spunbonded not gamma stabilized
B. 1.6 oz/yd$^2$ copolymer SMS not gamma stabilized
C. 1.8 oz/yd$^2$ copolymer SMS with gamma stabilizer
D. 1.8 oz/yd$^2$ hompolymer SMS with gamma stabilizer and an internal odor mask TABLE I-continued

FABRIC IDENTIFICATION KEY

E. 1.8 oz/yd$^2$ homopolymer SMS with gamma stabilizer
F. 1.8 oz/yd$^2$ homopolymer SMS with gamma stabilizer, untreated with an alcohol repellant
G. 1.6 oz/yd$^2$ homopolymer SMS not gamma stabilized Note:
The "homopolymer" is 100% polypropylene
The "copolymer" is 97% propylene/3% ethylene The oxygen scavenger used was in 2.5"×3" packets, some of which were able to absorb 400 cc of oxygen, and others capable of absorbing 1,000 cc of oxygen.

Three 1,000 cc packets were placed in bags containing the samples for a total of 3000 cc of oxygen absorption capability.

In addition, some of the samples were tested with lower levels of oxygen scavenger. Each of the 12 square yard samples were folded and then packaged in 20"×25" nylon/saran/polyethylene high barrier bags from Koch Supplies, and then heat sealed. Before heat sealing, as much air as possible was removed from the bags, however, the bags were not vacuum packed. The oxygen scavenger used throughout the study was FRESHPAX ® from Multiform Dessicants, Inc.

After the samples were irradiated, they were presented to panelists who evaluated the amount of odor resulting from each sample. The odor panelists were told to rate the fabrics for odor intensity on a scale of 0 to 5, with 0 being no odor at all, and 5 being highly offensive. It has previously been determined that an average odor rating of about 1.5 or less represents that the product being tested has an acceptable odor rating.

For each sample, the bag was opened and the fabric was spread out in a closed 10'×12'×9' room. The fabric was allowed to air-out in the room for one minute. The odor panelists were then allowed to enter the room, and the door was closed. The panelists then recorded what level, on a scale of 0 to 5, they perceived the odor to be. See Table 2.

TABLE 2

ODOR RATING AVERAGES
(Sterilized samples dosed at 6 megarads unless otherwise noted)

|   | NO OXYGEN SCAVENGER | 400 cc OXYGEN SCAVENGER | 1200 cc OXYGEN SCAVENGER | 3000 cc OXYGEN SCAVENGER |
|---|---|---|---|---|
| A | 3.36 |  |  | 0.94 |
| B | 3.27 |  |  | 0.23 |
| C | 3.85 |  |  | 1.15 |
| D | 2.75 | 2.60 | 1.28 | 0.25 |
| E | 2.63 | 3.71 | 1.71 | 0.00 |
| F | 4.05 |  |  | 1.05 |
| G | 3.08 |  | 0.47 | 1.00 |

Once odor panels had been completed on the samples, variations of the amount of oxygen scavenger used were tested on the polyolefin-based fabrics. The purpose of using different amounts of oxygen scavenger was to define a lower limit or threshold for the amount of scavenger needed to attain desired strength and odor goals based on the volume of air in the package. Each of these fabrics was then tested for strength measured in terms of grab tensile strength (ASTM D-5034), trapezoidal tear strength (ASTM D-1117), Mullen bursting strength (TAPPI T-403), and Elmendorf tear strength (ASTM D-1424). Full strength and odor results are represented in Tables 3–10.

TABLE 3

MD/CD Fabric Grab Tensile Strength
(Sterilized samples dosed at 6 megarads unless otherwise noted)

|   | PRE-STERILIZATION Peak Load | POST-STERILIZATION Peak Load-No. OS | POST-STERILIZATION Peak Load-400 cc OS | POST-STERILIZATION Peak Load-1200 - cc OS | POST-STERILIZATION Peak Load-3000 cc OS |
|---|---|---|---|---|---|
| A | 2.4/3.0 | 2.4/2.9 |  |  | 3.6/3.2 |
| B | 17.4/14.7 | 9.9/7.0 |  |  | 13.8/14.5 |
| C | 20.6/21.8 | 12.9/12.1 |  |  | 19.0/17.2 |
| D (Trial 1) | 23.9/21.0 | 17.1/13.9 | 16.7/12.5 | 18.2/18.6 | 18.7/14.9 |
| D (Trial 2) |  | 16.7/11.5 |  |  | 20.9/18.4 |
| D* |  | 17.7/17.3 |  | 22.3/14.9 |  |
| E (Trial 1) | 24.6/20.4 | 15.8/13.9 | 14.2/14.1 | 18.0/16.2 | 19.2/16.5 |
| E (Trial 2) |  | 13.7/12.6 |  |  | 20.6/17.1 |
| E* |  | 18.6/14.9 |  | 21.3/17.7 |  |
| F | 20.8/17.3 | 13.6/11.7 |  |  | 18.8/15.4 |
| G | 18.5/18.1 | 9.9/7.6 |  | 12.9/11.9 | 14.3/12.2 |

|   | PRE-STERILIZATION Peak Elong | POST-STERILIZATION Peak Elong-No. OS | POST-STERILIZATION Peak Elong-400 cc OS | POST-STERILIZATION Peak Elong 1200 - cc OS | POST-STERILIZATION Peak Elong. 3000 cc OS |
|---|---|---|---|---|---|
| A | 90.0%/103.4% | 111.6%/98.2% |  |  | 112.8%/111.2% |
| B | 36.8%/44.0% | 20.9%/24.0% |  |  | 41.6%/27.8% |
| C | 38.7%/43.4% | 28.8%/38.6% |  |  | 36.8%/49.4% |
| D (Trial 1) | 48.3%/42.0% | 32.3%/36.9% | 26.7%/32.4% | 33.8%/41.3% | 34.1%/36.5% |
| D (Trial 2) |  | 28.9%/31.2% |  |  | 36.9%/39.4% |

TABLE 3-continued

MD/CD Fabric Grab Tensile Strength
(Sterilized samples dosed at 6 megarads unless otherwise noted)

| | | | | | |
|---|---|---|---|---|---|
| D* | | 33.7%/41.3% | | 32.2%/37.0% | |
| E (Trial 1) | 40.4%/48.9% | 28.3%/35.8% | 25.9%/34.5% | 29.4%/37.9% | 32.0%/40.1% |
| E (Trial 2) | | 24.5%/32.1% | | | 31.8%/41.7% |
| E* | | 30.6%/38.6% | | 36.8%/41.7% | |
| F | 46.9%/59.5% | 33.4%/41.0% | | | 39.4%/45.5% |
| G | 37.2%/50.6% | 21.7%/22.4% | | 29.5%/35.0% | 31.4%/35.6% |

Peak load results are in pounds
Peak elongation results are % elongation from 3 inches.
All results are an average of 5 trials
*Dosed at 3 megarads
OS = Oxygen Scavenger

TABLE 4

MD/CD Fabric Gmb Tensile Strength Loss
(Relative to unsterilized fabric)

| | POST-STERILIZATION Peak Load-No. OS | POST-STERILIZATION Peak Load-400 cc OS | POST-STERILIZATION Peak Load-1200 cc OS | POST-STERILIZATION Peak Load-3000 cc OS |
|---|---|---|---|---|
| A | −0%/−3% | | | +50%/+6% |
| B | −43%/−52% | | | −21%/−1% |
| C | −37%/−44% | | | −8%/−21% |
| D (Trial 1) | −28%/−34% | −30%/−40% | −24%/−11% | −22%/−29% |
| D (Trial 2) | −30%/−45% | | | −13%/−12% |
| D* | −26%/−18% | | −7%/−29% | |
| E (Trial 1) | −36%/−32% | −42%/−30% | −27%−20% | −22%/−19% |
| E (Trial 2) | −44%/−38% | | | −16%/−16% |
| E* | −24%/−27% | | −13%/−13% | |
| F | −35%/−32% | | | −10%/−11% |
| G | −46%/−58% | | −30%/−34% | −23%/−33% |

| | POST STERILIZATION Peak Load-No. OS | POST-STERILIZATION Peak Load-400 cc OS | POST-STERILIZATION Peak Load-1200 cc OS | POST-STERILIZATION Elongation 3000 cc OS |
|---|---|---|---|---|
| A | +24%/−5% | | | +25%/+8% |
| B | −43%/−45% | | | +13%/−36% |
| C | −26%/−11% | | | −5%/+14% |
| D (Trial 1) | −33%/−12% | −45%/−23% | −30%/−2% | −29%/−13% |
| D (Trial 2) | −40%/−26% | | | −24%/−6% |
| D* | −30%/−2% | | −33%/−12% | |
| E (Trial 1) | −30%/−27% | −36%/−29% | −27%/−23% | −21%/−18% |
| E (Trial 2) | −39%/−34% | | | −21%/−15% |
| E* | −24%/−21% | | −9%/−15% | |
| F | −29%/−31% | | | −16%/−24% |
| G | −42%/−56% | | −21%/−31% | −16%/−30% |

*Dosed at 3 megarads

TABLE 5

MD/CD Fabric Trapezoidal Tear Strentgth
(Sterilized samples dosed at 6 megarads unless otherwise noted)

| | PRE-STERILIZATION Tear Mean | POST-STERILIZATION Tear Mean-No. OS | POST-STERILIZATION Tear Mean-400 cc OS | POST-STERILIZATION Tear Mean-1200 cc OS | POST-STERILIZATION Tear Mean-3000 cc OS |
|---|---|---|---|---|---|
| A | 1.82/1.09 | 1.23/0.98 | | | 1.48/1.21 |
| B | 3.06/2.75 | 0.86/0.64 | | | 1.96/2.10 |
| C | 4.58/4.35 | 2.07/1.78 | | | 3.89/3.12 |
| D (Trial 1) | 3.77/4.78 | 1.86/1.57 | 2.11/2.00 | 3.40/2.81 | 2.96/2.37 |
| D (Trial 2) | | 2.08/1.60 | | | 3.36/3.64 |
| D* | | 2.60/2.78 | | 3.64/3.31 | |
| E (Trial 1) | 3.93/3.18 | 1.86/1.70 | 1.86/1.55 | 2.66/2.50 | 2.78/2.24 |

TABLE 5-continued

MD/CD Fabric Trapezoidal Tear Strentgth
(Sterilized samples dosed at 6 megarads unless otherwise noted)

|   |   |   |   |   |   |
|---|---|---|---|---|---|
| E (Trial 2) |   | 1.88/1.91 |   |   | 3.55/2.73 |
| E* |   | 2.94/2.09 |   | 3.24/3.05 |   |
| F | 4.30/3.58 | 2.02/2.03 |   |   | 2.95/2.57 |
| G | 3.66/3.15 | 1.30/0.93 |   | 2.64/3.18 | 1.64/1.51 |

|   | PRE-STERILIZATION Avg. 1st + high | POST-STERILIZATION Avg. 1st + high No OS | POST-STERILIZATION Avg.1st + high −400 cc OS | POST-STERILIZATION Ave.1st + high 1200 cc OS | POST-STERILIZATION Avg.1st + high− 3000 cc OS |
|---|---|---|---|---|---|
| A | 4.07/2.11 | 2.47/1.82 |   |   | 3.96/2.29 |
| B | 6.55/5.74 | 2.17/1.48 |   |   | 4.15/4.53 |
| C | 9.14/8.78 | 4.37/3.58 |   |   | 8.31/5.91 |
| D (Trial 1) | 8.03/10.49 | 4.30/3.46 | 4.00/3.64 | 6.22/5.12 | 6.63/5.05 |
| D (Trial 2) |   | 4.88/3.96 |   |   | 6.47/7.17 |
| D* |   | 5.14/5.86 |   | 6.47/6.60 |   |
| E (Trial 1) | 8.51/7.33 | 4.11/3.60 | 3.53/3.10 | 4.97/4.71 | 5.94/4.80 |
| E (Trial 2) |   | 3.89/4.04 |   |   | 6.44/5.17 |
| E* |   | 6.04/4.14 |   | 6.15/5.49 |   |
| F | 9.12/7.34 | 4.64/4.48 |   |   | 6.30/5.73 |
| G | 6.88/5.96 | 3.04/2.15 |   | 5.42/4.34 | 3.72/3.51 |

All results are in pounds
All results are an average of 5 trials
*Dosed at 3 megarads

TABLE 6

MD/CD Trapezoidal Tear Strength Loss
(Relative to unsterilized fabric)

|   | POST-STERILIZATION Tear Mean-No. OS | POST STERILIZATION Tear Mean-400 cc OS | POST STERILIZATION Tear Mean-1200 cc OS | POST-STERILIZATION Tear Mean 3000 cc OS |
|---|---|---|---|---|
| A | −32%/−10% |   |   | −19%/+11% |
| B | −72%/−77% |   |   | −36%/−24% |
| C | −55%/−59% |   |   | −15%/−28% |
| D (Trial 1) | −51%/−62% | −44%/−58% | −10%/−41% | −22%/−50% |
| D (Trial 2) | −45%/−67% |   |   | −11%/−24% |
| D* | −31%/−42% |   | −32%/−21% |   |
| E (Trial 1) | −53%/−47% | −53%/−51% | −59%/−58% | −29%/−30% |
| E (Trial 2) | −52%/−40% |   |   | −10%/−14% |
| E* | −25%/−34% |   | −42%/−36% |   |
| F | −53%/−43% |   |   | −31%/−28% |
| G | −65%/−71% |   | −28%/+1% | −55%/−52% |

|   | POST-STERILIZATION Avg. 1st + high No OS | POST-STERILIZATION Avg. 1st + high −400 cc OS | POST-STERILIZATION Avg. 1st + high 1200 cc OS | POST-STERILIZATION Avg.1st + high 3000 cc OS |
|---|---|---|---|---|
| A | −39%/−14% |   |   | −3%/+9% |
| B | −67%/−74% |   |   | −37%/−21% |
| C | −52%/−59% |   |   | −9%/−33% |
| D (Trial 1) | −47%/−67% | −50%/−65% | −23%/−51% | −17%/−52% |
| D (Trial 2) | −39%/−62% |   |   | −19%/−32% |
| D* | −36%/−44% |   | −19%/−37% |   |
| E (Trial 1) | −52%/−51% | −59%/−58% | −42%/−36% | −30%/−35% |
| E (Trial 2) | −54%/−45% |   |   | −24%/−29% |
| E* | −29%/−44% |   | −28%/−25% |   |
| F | −49%/−39% |   |   | −31%/−22% |
| G | −56%/−64% |   | −21%/−27% | −46%/−41% |

*Dosed at 3 megarads

TABLE 7

MD/CD Fabric Elmendorf Tear Strentgth
(Sterilized samples dosed at 6 megarads)

|   | PRE-STERILIZATION | POST-STERILIZATION No OS | POST-STERILIZATION 400 cc OS | POST-STERILIZATION 1200 cc OS | POST-STERILIZATION 3000 cc OS |
|---|---|---|---|---|---|
| B | 640/551 | 244/212 | | | 352/388 |
| C | 816/812 | 408/352 | | | 616/494 |
| D (Trial 1) | 780/736 | 412/404 | 390/384 | 525/403 | 500/448 |
| D (Trial 2) | | 348/332 | | | 460/404 |
| E (Trial 1) | 736/752 | 308/292 | 378/371 | 410/442 | 508/388 |
| E (Trial 2) | | 364/344 | | | 448/436 |
| F | 717/586 | 288/276 | | 512/416 | |
| G | 744/755 | 346/364 | | 442/467 | |

All results are in grams
Results are an average of 5 trials for some, 8 trials for others

TABLE 8

Fabric Mullen Burst Strength
(Sterilized samples dosed at 6 megarads)

|   | PRE-STERILIZATION | POST-STERILIZATION No OS | POST-STERILIZATION 400 cc OS | POST-STERILIZATION 1200 cc OS | POST-STERILIZATION 3000 cc OS |
|---|---|---|---|---|---|
| B | 24.4 | 10.7 | | | 24.4 |
| C | 32.0 | 20.6 | | | 29.6 |
| D (Trial 1) | 33.9 | 23.9 | 22.8 | 28.5 | 26.5 |
| D (Trial 2) | | 23.8 | | | 27.8 |
| E (Trial 1) | 31.3 | 20.3 | 21.0 | 26.5 | 28.5 |
| E (Trial 2) | | 20.7 | | | 29.8 |
| F | 28.4 | 20.9 | | | 29.5 |
| G | 34.9 | 20.5 | | | 25.6 |

All results are in lbs/sq. inch
Results are an average of 12 trials, except group G (5 trials)

TABLE 9

MD/CD Elmdorf Tear Strength Loss
(relative to unsterilized fabric)

|   | POST-STERILIZATION No OS | POST-STERILIZATION 400 cc OS | POST-STERILIZATION 1200 cc OS | POST-STERILIZATION 3000 cc OS |
|---|---|---|---|---|
| B | −62%/−62% | | | −45%/−30% |
| C | −50%/−57% | | | −25%/−40% |
| D (Trial 1) | −47%/−45% | −50%/−48% | −33%/−45% | −36%/−39% |
| D (Trial 2) | −55%/−55% | | | −41%/−45% |
| E (Trial 1) | −58%/−61% | −49%/−51% | −44%/−41% | −35%/−47% |
| E (Trial 2) | −51%/−54% | | | −39%/−42% |
| F | −60%/−53% | | | −30%/−29% |
| G | −54%/−52% | | | −41%/−48% |

TABLE 10

Mullen Burst Strength Loss
(relative to unsterilized fabric)

|   | POST-STERILIZATION No OS | POST-STERILIZATION 400 cc OS | POST-STERILIZATION 1200 cc OS | POST-STERILIZATION 3000 cc OS |
|---|---|---|---|---|
| B | −56% | | | −0% |
| C | −36% | | | −8% |
| D (Trial 1) | −30% | −33% | −16% | −22% |
| D (Trial 2) | −30% | | | −18% |
| E (Trial 1) | −35% | −33% | −15% | −9% |

TABLE 10-continued

| | Mullen Burst Strength Loss (relative to unsterilized fabric) | | | |
|---|---|---|---|---|
| | POST-STERILIZATION No OS | POST-STERILIZATION 400 cc OS | POST-STERILIZATION 1200 cc OS | POST-STERILIZATION 3000 cc OS |
| E (Trial 2) | −34% | | | −5% |
| F | −26% | | | +4% |
| G | −41% | | | −27% |

It is important to note that the bulk of the fabrics used in this study were sterilized at 6 MRADS. Typically, polyolefin containing surgical gowns used in hospitals are sterilized at between 2 and 2.25 MRADS. However, some polyolefin-based surgical products are sterilized at 6 MRADS. Because increased MRADS cause decreased polyolefin strength and potentially increased levels of odors, the 6 MRAD radiation dosage used in this study had the potential to cause both an increase in the level of odors, and an increase in strength loss caused by normal radiation. However, the tests demonstrate that even under these extreme conditions the invention functions to decrease both odors and strength loss.

A. ODOR RESULTS

The samples that contained oxygen scavenger received significantly lower odor ratings than samples without oxygen scavenger in all the odor panels. See Table 2. The panelists rated the fabrics without an oxygen scavenger as highly offensive, with an average odor rating of nearly 3.5 on a 5 point scale. When 3000 cc of oxygen scavenger were used, the average odor rating was below 1.0. As previously indicated, an average odor rating below 1.5 is acceptable. Therefore, an average rating of below 1.0 is indicative of very favorable results. Every fabric tested using an oxygen scavenger was rated as having a significantly lower odor rating than the same fabrics without the oxygen scavenger.

In the odor panels, it was found that the homopolymer with odor mask did not perform better than homopolymer without odor mask. See Table 2. Both fabrics had nearly the same odor ratings at all oxygen scavenger levels, including one with no oxygen scavenger.

Another interesting finding was that the use of activated carbon as an odor scavenger in conjunction with the oxygen scavenger did not significantly reduce odor. Two samples were used with activated carbon and 400 cc of oxygen scavenger. Neither of these samples was rated lower in the odor panels than 400 cc of oxygen scavenger alone. See Table 2, columns D and E.

Although the use of 3000 cc of oxygen scavenger proved to be very effective in reducing odor, the cost of using this much FRESHPAX ® scavenger is relatively high. It was therefore necessary to attempt to find a lower amount of scavenger that would perform as effectively as 3000 cc of scavenger. It was found that 1200 cc of oxygen scavenger performed nearly as well as 3000 cc of oxygen scavenger in the same previously defined bags. See Table 2. The odor ratings given by the panelists were in the 1 to 2 range for fabrics with 1200 cc of oxygen scavenger. A different panel was used for these tests and it will be recognized that some variation may be expected due to the experience level of the individual panelists. In this case, it is therefore believed that the actual odor ratings for the fabrics with 1200 cc of oxygen scavenger with a panel equivalent to the previous one may be actually below 1.0.

In an effort to ascertain the minimum amount of scavenger that would yield acceptable odor levels, some of the fabrics were also tested with 400 cc of oxygen scavenger. The panelists rated these fabrics as being quite high. Thus, it is believed that the minimum amount of oxygen scavenger needed to reduce the odors to an acceptable level is greater than 400 cc of oxygen scavenger for the test package used. See Table 2.

One particularly encouraging result of the odor panels was the performance of unstabilized materials when used with oxygen scavenger. Previously it was believed that polyolefin fabrics needed to be gamma stabilized during fabric formation in order to prevent the high rating of post-gamma irradiation odor. However, when 3000 cc of oxygen scavenger was used, both the unstabilized homopolymer and the stabilized copolymer received odor ratings around 1.0. The unstabilized homopolymer also received an odor rating below 1.0 when used with only 1200 cc of oxygen scavenger. See Table 2. These results of the unstabilized materials are important due to the cost-effectiveness of not having to use a gamma-stabilizer, which, in turn, significantly reduces the cost of producing the polyolefin-based fabrics.

B. STRENGTH RESULTS

In addition to the odor tests, various strength tests were performed on the gamma irradiated fabrics. Quite a few interesting discoveries were made in the strength evaluation. The most interesting discovery was of the effect the oxygen scavenger had on the strength of spunbonded polyethylene. There was no difference in the strength of the unsterilized sample of polyethylene and the sample that was radiated without oxygen scavenger. However, when polyethylene was sterilized and 3000 cc of oxygen scavenger was used, there was a strength gain of nearly 40% over the polyethylene prior to its irradiation. (MD=machine direction; CD=cross direction)

| Fabric | Pre-sterilized | No $O_2$ Scavenger | 3000 cc $O_2$ Scavenger |
|---|---|---|---|
| Potyethytene | 2.4 MD/3.0 CD | 2.4 MD/2.9 CD | 3.6 MD/3.2 CD |

Another notable result from the strength testing was that there was no significant strength difference between a homopolymer with an odor mask and a homopolymer without an odor mask. See Tables 3–10. Given that an odor mask did not provide significant advantages in preventing odor, it is not believed to be a component that is absolutely necessary to achieve acceptable results. Both polypropylene homopolymers fabrics lost about 40% of their pre-sterilized strength when no oxygen scavenger was used. When 3000 cc of oxygen scavenger were used, this strength loss was reduced to about 20%. The strength loss was also only about 20% when 1200 cc of oxygen scavenger were used. In comparing strength and odor qualities, 1200 cc of scavenger appeared to perform as well as 3000 cc of scavenger. When these fabrics were tested with only 400 cc of scavenger, strength losses were in the 30%-40% range.

mopolymer fabrics was approximately 25%, which was significantly less than the strength loss associated with 6 MRADS. The homopolymer fabrics irradiated with 3 MRADS lost only 15% of their strength when sterilized in the presence of 1200 cc of oxygen scavenger. In addition, the 3 MRAD fabrics had nearly negligible odor with oxygen scavenger.

| Fabric | Pre-sterilized | No O$_2$ Scavenger | 400 CC O$_2$ Scavenger | 1200 cc O$_2$ Scavenger | 3000 cc O$_2$ Scavenger |
|---|---|---|---|---|---|
| Homopolymer w/odor mask | 23.9 MD/21.0 CD | 17.1 MD/13.9 CD | 16.7 MD/12.5 CD | 18.2 MD/18.6 CD | 18.7 MD/14.9 CD |
| Homopolymer | 24.6 MD/20.4 CD | 15.8 MD/13.9 CD | 14.2 MD/14.1 CD | 18.0 MD/16.2 CD | 19.2 MD/16.5 CD |

It therefore appears that greater than 400 cc of oxygen scavenger must be used to reduce post-irradiation strength loss such that the product strength is within an acceptable range.

In comparing the strength of the homopolymer and the copolymer, non-sterilized homopolymer was generally about 20% stronger than the non-sterilized copolymer. However, the post-sterilization strength losses were greater in the homopolymer than the copolymer. Because the copolymer did not lose as much strength, the strength of the homopolymer and copolymer was about the same when both irradiated fabrics were packaged with 3000 cc of scavenger.

| Fabric | No O$_2$ Scavenger | 1200 cc O$_2$ Scavenger |
|---|---|---|
| Homopolymer w/odor mask | 17.7 MD/17.3 CD | 22.3 MD/14.9 CD |
| Homopolymer | 18.6 MD/14.9 CD | 21.3 MD/17.7 CD |

Turning to the Figure, a bag 10 is illustrated which may be used, for example, for packaging individual surgical products, such as gowns, drapes and packs. As shown, bag 10 comprises outer barrier layers 12, 14 which are gas impermeable and sealed, for example, by means of heat seal lines 16, 18, and 20. An internal pouch 22 is formed by gas permeable layer 24 which

| Fabric | Pre-sterilized | No O$_2$ Scavenger | 3000 cc O$_2$ Scavenger |
|---|---|---|---|
| Homopolymer | 24.6 MD/20.4 CD | 15.8 MD/13.9 CD | 19.2 MD/16.5 CD |
| Copolymer | 20.6 MD/21.8 CD | 12.9 MD/12.1 CD | 19.0 MD/17.2 CD |

The unstabilized fabrics were not as strong as their corresponding gamma stabilized fabrics. Taking into account their basis weights (that is, if the unstabilized materials had been 1.8 ounce per square yard), the unstabilized fabrics were approximately 15% weaker than the stabilized fabrics. When sterilized without oxygen scavenger, both the unstabilized homopolymer and unstabilized copolymer lost nearly 50% of their initial strength. The use of 3000 cc of oxygen scavenger reduced the strength loss in the unstabilized materials. The unstabilized copolymer strength loss was reduced to about 20% with 3000 cc of oxygen scavenger. However, the strength loss for both 1200 cc and 3000 cc of oxygen scavenger in the unstabilized homopolymer was still nearly 30%. At a 1.6 ounce per yard basis weight of fabric and 1200 cc of oxygen scavenger, the strength of the unstabilized materials was well below that of the corresponding stabilized materials. Where strength losses approach or exceed 50% of the pre-irradiated product, the commercial value of the product is considerably reduced.

may be sealed to both gas impermeable layers along lines 16 and 18 by means of the same heat seals but is sealed only to one impermeable layer, such as 12, along line 28 so that the pouch contents, scavenger 26, is exposed to the gas inside bag 10. In use, the product 29 to be sterilized is loaded through product loading end 30 after seal lines 16, 18, 20 and 28 have been formed. At about the same time, scavenger 26 is loaded into pouch 22, and a final seal line may then be formed closing product loading end 30. The pouch contents are non-obvious to the ultimate user yet have full access to the product to be sterilized. If desired, notches 34 may be cut in product removal end edges to facilitate product removal.

Thus, while methods for reducing odors and strength loss caused by the irradiation of polyolefin-based products, carrier means to effect same, the products of the methods, and modifications thereof have been shown and described in detail herein, various additional changes and modifications may be made without departing from the scope of the present invention.

| Fabric Scavenger | Pre-sterilized | No O$_2$ Scavenger | 3000 cc O$_2$ |
|---|---|---|---|
| Unstabilized homopolymer | 17.4 MD/14.7 CD | 9.9 MD/7.0 CD | 13.8 MD/14.5 CD |
| Unstabilized copolymer | 18.5 MD/18.1 CD | 9.9 MD/7.6 CD | 14.3 MD/12.2 CD |

Two samples that performed well in both strength and odor were the homopolymer and homopolymer with odor mask dosed at 3 MRADS. When sterilized without oxygen scavenger, the strength loss in the ho-

We claim:

1. A method for reducing the undesirable side effects associated with the irradiation of a polyolefin-based product comprising the step of exposing said polyolefin-based product to an oxygen scavenger, both of which are in or a part of a sealed container prior to said irradiation.

2. A method for reducing odors associated with the sterilization by irradiation of polyolefin-based products comprising the steps of:
   a) inserting a polyolefin-based product into an oxygen impermeable sealable bag;
   b) inserting an oxygen scavenger into said bag;
   c) sealing said bag to prevent air from either entering or escaping said bag; and
   d) sterilizing said sealed bag and its contents with gamma radiation.

3. The method of claim 2, wherein said polyolefin-based product includes an odor mask.

4. The method of claim 2, wherein said method further comprises evacuating substantially all of the air from said bag prior to sealing said bag.

5. The method of claim 2, wherein said polyolefin-based product is a homopolymer.

6. The method of claim 2, wherein said polyolefin-based product is a copolymer.

7. The method of claim 2, wherein said polyolefin-based product comprises a fabric.

8. The method of claim 2, wherein said polyolefin-based product further comprises a gamma stabilizer.

9. The method of claim 2, wherein said method further comprises inserting an odor scavenger into said bag prior to sealing said bag.

10. The method of claim 2, wherein said oxygen scavenger is contained in a carrier means.

11. The method of claim 2, wherein said oxygen scavenger is connected to a carrier means.

12. A polyolefin-based product that has been sterilized according to the method of claim 2.

13. A method for reducing strength loss associated with the sterilization of a polyolefin-based product that has a pre-sterilization strength comprising the steps of:
   a) inserting a polyolefin-based product into an oxygen impermeable sealable bag;
   b) inserting an oxygen scavenger into said bag;
   c) sealing said bag to prevent air from either entering or escaping said bag; and
   d) sterilizing said sealed bag and its contents with gamma radiation.

14. The method of claim 13, wherein said method further comprises evacuating as much air as possible from said bag prior to sealing said bag.

15. The method of claim 13, wherein said polyolefin-based product is a homopolymer.

16. The method of claim 13, wherein said polyolefin-based product is a copolymer.

17. The method of claim 13, wherein said polyolefin-based product comprises a fabric.

18. The method of claim 13, wherein said polyolefin-based product further comprises a gamma stabilizer.

19. The method of claim 13, wherein said method further comprises inserting an odor scavenger into said bag prior to sealing said bag.

20. The method of claim 13, wherein said oxygen scavenger is contained in a carrier means.

21. The method of claim 13, wherein said oxygen scavenger is connected to a carrier means.

22. A polyolefin-based product that has been sterilized according to the method of claim 13.

23. A method for increasing the strength of a polyethylene-based product comprising:
   a) exposing said polyethylene-based product to an oxygen scavenger, both of which are contained in an oxygen impermeable package; and
   b) gamma-irradiating said package and said product such that the strength of said product is greater than the prior-to-irradiation strength thereof.

24. A polyethylene-based product that has been sterilized according to the method of claim 23.

25. A method for preventing the formation of oxygenated compounds that are formed after a polyolefinic product is exposed to gamma radiation in the presence of oxygen comprising the steps of placing said polyolefinic product and an oxygen scavenger in a sealed container and irradiating said product and container with gamma radiation at a level of exposure sufficient to sterilize said product.

* * * * *